United States Patent
Opie et al.

(10) Patent No.: US 7,494,010 B2
(45) Date of Patent: Feb. 24, 2009

(54) RACE GUIDE WIRE CONTAINER

(75) Inventors: John C. Opie, Scottsdale, AZ (US);
Stephen J. Joyce, Phoenix, AZ (US);
Thomas Izdebski, Phoenix, AZ (US)

(73) Assignee: JS Vascular, Inc., Scottsdale, AZ (US)

( * ) Notice: Subject to any disclaimer, the term of this patent is extended or adjusted under 35 U.S.C. 154(b) by 430 days.

(21) Appl. No.: 10/861,889

(22) Filed: Jun. 3, 2004

(65) Prior Publication Data
US 2005/0040061 A1 Feb. 24, 2005

Related U.S. Application Data

(60) Provisional application No. 60/475,606, filed on Jun. 3, 2003.

(51) Int. Cl.
*B65D 83/10* (2006.01)
(52) U.S. Cl. .................. 206/363; 206/303; 600/585

(58) Field of Classification Search .................. 206/303, 206/363, 364, 408, 438; 604/159; 600/585
See application file for complete search history.

(56) References Cited

U.S. PATENT DOCUMENTS

| | | | | |
|---|---|---|---|---|
| 3,995,628 | A * | 12/1976 | Gula et al. | 604/159 |
| 4,342,313 | A * | 8/1982 | Chittenden | 604/159 |
| 4,903,826 | A * | 2/1990 | Pearce | 206/63.3 |
| 5,125,906 | A * | 6/1992 | Fleck | 604/171 |
| 5,131,534 | A * | 7/1992 | Brown et al. | 206/63.3 |
| 5,344,011 | A * | 9/1994 | DiBernardo et al. | 206/364 |
| 5,366,444 | A * | 11/1994 | Martin | 604/159 |
| 5,454,785 | A * | 10/1995 | Smith | 604/510 |
| 5,843,002 | A * | 12/1998 | Pecor et al. | 600/585 |
| 7,070,044 | B2 * | 7/2006 | Rosenfeld | 206/63.3 |
| 2003/0036712 | A1 * | 2/2003 | Heh et al. | 600/585 |

* cited by examiner

*Primary Examiner*—David T Fidei
(74) *Attorney, Agent, or Firm*—Fennemore Craig, P.C.

(57) ABSTRACT

Disclosed is a race guide wire containment and dispensing system comprising an outer housing and an inner housing.

5 Claims, 9 Drawing Sheets

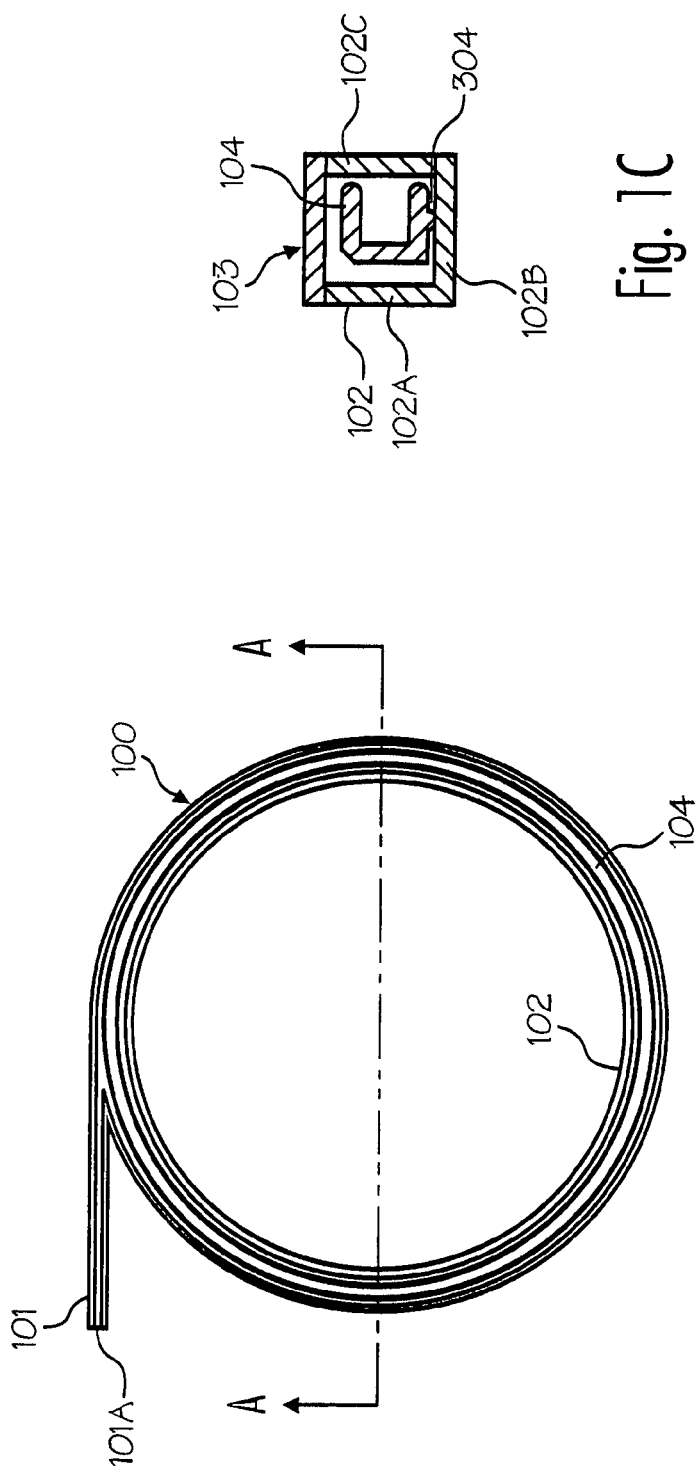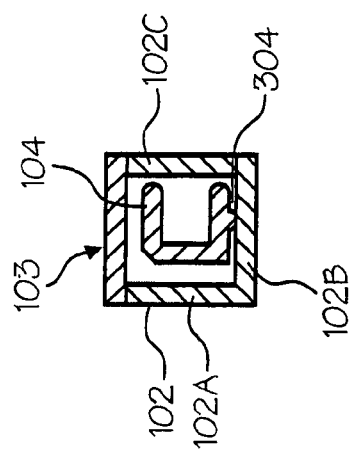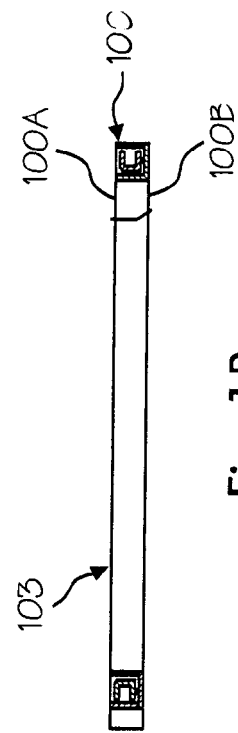
Fig. 1A
Fig. 1B
Fig. 1C

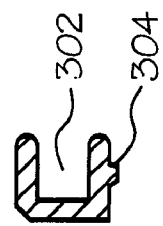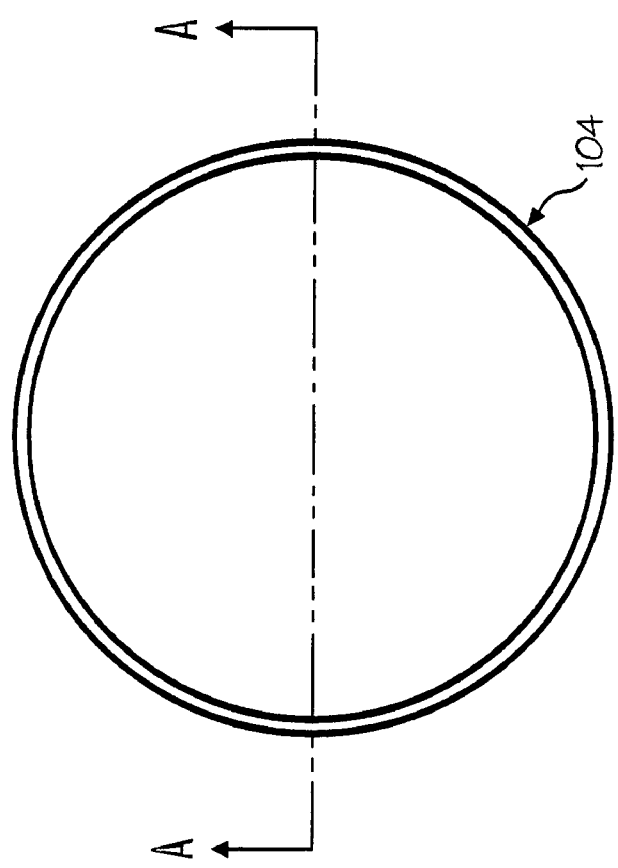

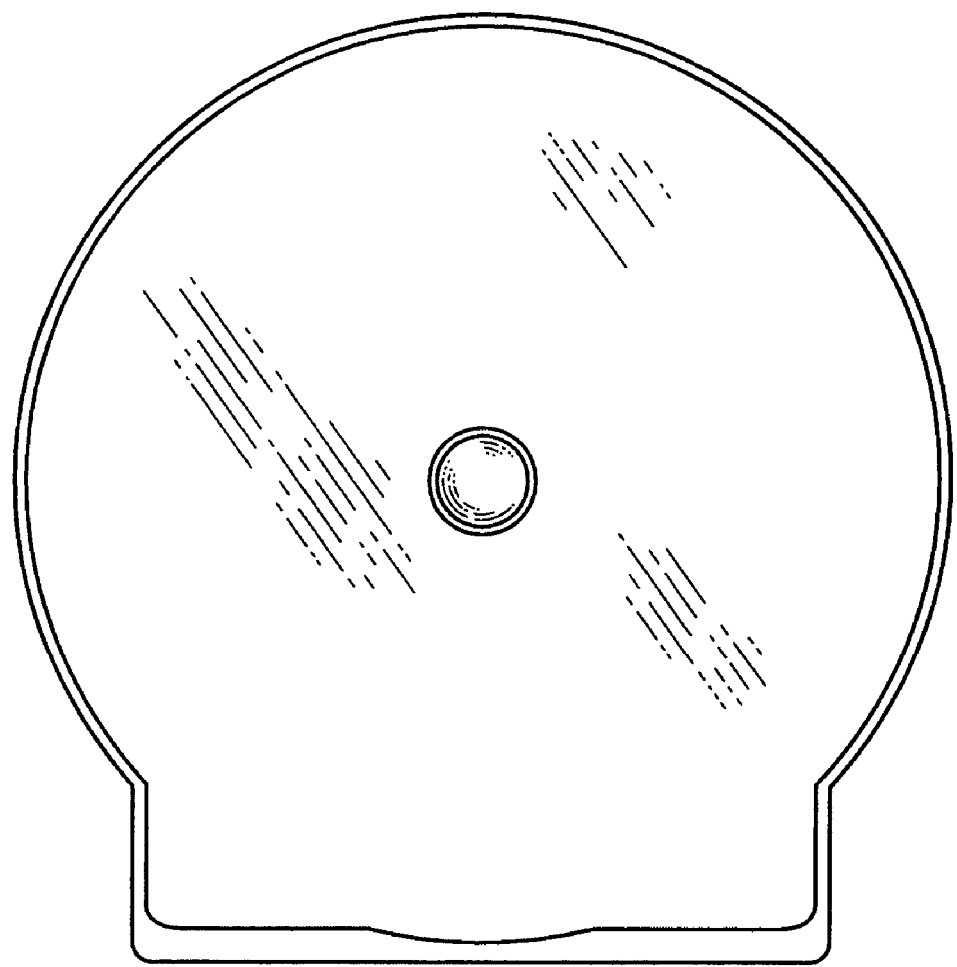

RACE GUIDE WIRE CONTAINER

RELATED APPLICATIONS

This application claims priority to U.S. Provisional Application Ser. No. 60/475,606, filed Jun. 3, 2003. The disclosure of U.S. application Ser. No. 10/444,773, filed May 24, 2003 and entitled "Guide Wire Torque Device," and U.S. patent application Ser. No. 10/861,888 filed Jun. 3, 2004 and entitled "Medical Guide Wires," is herein incorporated by reference.

TECHNICAL FIELD OF THE INVENTION

This invention relates to the field of medical devices and, more specifically, to a race medical guide wire containment system.

BACKGROUND OF THE INVENTION

The use of medical guide wires (or "guide wires") is ubiquitous in modern era, non-invasive, medical practice including cardiac catheterization and interventional radiology disciplines and the practice of endo-vascular surgery.

An accepted method of accessing the interior of a blood vessel involves placing a needle inside a short cannula, and then placing the needle and cannula into the blood vessel with subsequent extraction of the needle, but retention of the short cannula. This method is used for both diagnostic and endo-vascular surgical procedures. Once the needle is removed from the blood vessel, the cannula becomes an open access to the vasculature and blood will escape through the cannula unless the cannula is capped. Once a cannula has been placed in a blood vessel using this or any other method, it is common for a general-purpose guide wire, such as a 0.018-inch diameter wire or a flexible, 0.035 inch×4.5 mm regular J guidewire (which, as known to those skilled in the art is a guide wire having a single, J-shaped, flexible tip of 4.5 mm in length) to be inserted into the cannula and into the blood vessel. At that point, the cannula is removed leaving the guide wire in the blood vessel an extending outward through percutaneous puncture. The intra-vascular location of the guide wire is usually confirmed with fluoroscopy or other suitable method at this point.

Once confirmed that the guide wire is intra-vascular, a sheath and dilator may be passed over the guide wire. The dilator is then removed and the sheath is flushed with heparin. Once that is completed, a guide wire exchange may be made, whereby the general-purpose guide wire may be replaced with another guide wire. The new guide wire may be a long J guide wire, a long regular or firm, angled or straight, 0.035 inch guide wire or a long similar featured floppy-tipped stiff guide wire depending upon the physician, choice, and of any length that may be desired by the physician to accomplish whatever goal is required. On occasions for example in selected intra-aortic procedures, a very stiff wire, sometimes called a "coat-hanger" wire, such as a Lindquist or Amplatz wire is selected (for endo-vascular repair of an abdominal aortic aneurysm for example.)

Most medical guide wires presently come prepackaged in a single use sterile pack consisting of an outer layer on one side of the sterile pack, of white backing paper that is rugged and difficult to tear, and on the other side, transparent, non-tearable cellophane. The cellophane and the white backing paper are heat-sealed and at one end, a peelable seal is made. To open the sterile pack, the chevron seal is grasped between both hands and the two sheets of paper are peeled apart. The medical guide wire is then passed from the sterile pack to the operator.

Presently, a single medical grade guide wire is stored in a circular coil of a capillary plastic tube sufficient to contain the length of the guide wire that has been selected. Typically, the capillary tube is coiled and is four or five spirals wide (especially when longer guide wires are packaged). The wire resides within the lumen of the spiraled capillary tube. Each pass of the capillary tube passes inside its previous spiral and so on until the spiral stops at some point. Frequently, there is a separate 4-5 inch single tubular section of additional coil to restrain the end of the wire clipped inside the rest of the coil. Each coil of tube can move independently of the other coils of the tube. Thus, it is necessary to restrain the independent movement of each individual coil of the tube, which is typically accomplished by fastening the coils together with a plurality of individual, multi-toothed clips. Each clip typically has between 4 and 5 C-shaped extensions or teeth that are manually snapped or clipped onto each individual coil to hold the coils in place.

This system has several drawbacks. For example, the coils are easily deformable, thus the necessity of manually placing the clips onto the coils, and this process is labor and cost intensive. Also, the clips can and do come loose and thus the coiled tube may become uncoiled thereby threatening sterility during both use and transport, or the tube may simply become difficult to use in the operating room. Additionally, when the clipped, multi-coiled tube is gripped by the hand the coils tend to collapse on each other and the palm is not large enough to maintain a sufficient grip when that happens. This can and does complicate the removal of the guide wire from the tube. Additionally, it is necessary with this type of wire containment system to have an assembly line of workers placing individual clips symmetrically about the coiled capillary plastic tubing either before or after inserting the guidewire. In addition, the plastic coil itself has to be extruded and then coiled before the clips can be applied. This type of containment system is labor intensive and therefore expensive to produce and clinically uncomfortable to use because the system is not designed with any ergonomic considerations.

Also, when removing the guide wire, the inner surface of the coiled plastic tubing and the guide wire bind with considerable friction and it is necessary to inject saline into the plastic tubing to reduce the friction and make extraction of the wire easier. Even when this is done the wire still has a tendency to bind and can be difficult to remove from the tube. Further, it is usually impractical to reinsert the guide wire into the plastic tube because the tube wall binds with the outer coil of the guide wire and friction prevents the wire from being reloaded. So, once the guide wire is removed from the tube, if not immediately used, the wire is placed in a bowl of saline under a laparotomy sponge or is simply placed under a wet lap until required. Sometimes during these procedures, the guide wire will spring loose and can become unsterile necessitating a new wire.

SUMMARY OF THE INVENTION

The present invention relates to a containment and dispensing device for medical guide wires. The present invention is directed to a device that allows for a guide wire to be placed in a containment/dispenser system that is designed to simplify production methods, reduce overall production costs and, because it is ergonomically designed and easier to use.

The device is essentially a race and a raceway, both of which are preferably contained within a body (or the raceway itself may be the body). As used herein, "raceway" means a groove or track on which or in which a race is contained and may move. "Race" refers to a structure that is contained on or in the raceway and that moves independent of, and on or in the raceway when the proper directional force is applied. In the preferred embodiment, the raceway is positioned in a container (or body), and can be molded or otherwise formed as part of the body or may be formed separately and attached to the body. The body (which may be any shape) preferably contains one circular (as used herein, the term "circular" means any substantially circular shape) raceway preferably containing strategically placed projections. A race is positioned at least partially in the raceway and rides against one or more of the projections. The race and the raceway are enclosed by the body.

The race device is loaded with a guide wire by inserting the guide wire into the stop on the race and applying force to the guide wire which moves the race along the raceway. As the race moves, guide wire is deposited in the raceway.

The raceway projections promote low friction for the turning race as the wire is fed in or taken out. By this method friction is reduced as compared to simply pushing the guide wire into a circular or spiral container.

The device also preferably includes a handle and a wire torque device mount The device is preferably manufactured of a plastic polymer, such as a polycarbonate. The device can be used in a cabinet dispenser system that is capable of automatic real time online product inventory control and tracking, useful for both the supplier and the user facility.

BRIEF DESCRIPTION OF THE DRAWINGS

FIG. 1*a-c* are views of preferred embodiments of the invention.

FIG. 3*a*-3*c* are views of the inner housing of the invention; and

FIG. 10 shows, in accordance with an exemplarily embodiment of the present invention, a device body similar to a CD Jewel case.

DETAILED DESCRIPTION OF PREFFERED EMBODIMENTS

Figure 2C:
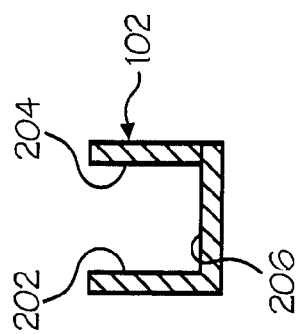
FIG. 2*a*-2*c* are views of preferred embodiments the outer housing of the invention.

As shown in FIG. 1, a race guide wire containment device 100 is generally circular, made of plastic, and has a generally flat top surface 100A and a generally flat bottom surface 100B (best seen in FIG. 1B), although any type of suitable surface or outer structure may be utilized. For example, the device may be square. Device 100 has a handle 101 and an opening 101A.

A raceway, or outer housing, 102 is preferably a generally annular track that is formed as part of device 100 although outer housing 102 could be a track within a larger housing. The purpose of raceway 102 is to Lid 103 can be a snap on, screw on, latch on or other type lid. Lid 103 may be hinged on one side and move about the hinge.

Projections may be formed on one or more of inner walls 202, 204 or 206 to help reduce friction between inner housing 104 and outer housing 102 as the inner housing rotates. Alternatively, the projections may be on the inner housing as shown, for example, in FIG. 3C. Also, a groove may be present in outer housing 102 to mate with inner housing 104 projections, or vice versa, in order to guide inner housing 104.

Figure 2B:
Figure 2A:
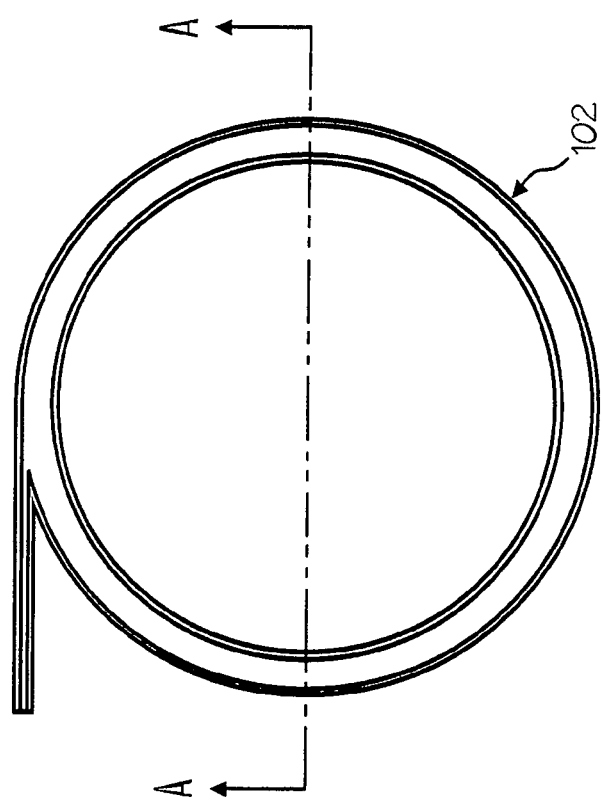

Inner housing 104, as best seen in FIGS. 3*a*-3*b*, is preferably of a similar shape as outer housing 102, e.g., preferably C-shaped, a track within a larger housing. The purpose of raceway 102 is to (a) provide a place to receive a guide wire, and (b) guide the race, as described below. Outer housing 102 could be of any shape or dimension suitable of its intended purpose, but as shown it has a generally rectangular construction with three walls 102A, 102B and 102C and an open end. Raceway 102 is generally circular and defines an annular cavity 102D. A top, or lid, 103 is placed on raceway 102 once race 104 is placed in position. Lid 103 is any suitable structure for covering annular cavity 102D and lid 103 may be attached to or positioned on raceway 102 using any suitable technique. Raceway 102 also has inner walls 202, 204 and 206. Outer housing 102 is dimensioned to receive the race, or inner housing 104. As best seen in FIGS. 2*a*-2*c*, outer housing 102 includes side walls 202 and 204 and a base 206. Race 104, which lies enclosed in the raceway 102, is sufficiently wide enough to permit the spiraling of multiple winds of wires.

Inner housing 104 is for moving a guide wire around the raceway and allowing the guide wire to be deposited in the raceway and any shape or dimension of race suitable for this purpose may be used. Inner housing 104 preferably has three walls 104A, 104B and 104C. Housing 104 defines a cavity 302 and has a projection 304, which rides on surface 206 of outer housing 102. Opening 302 in inner housing 104 receives one or more guide wires. Inner housing 104 may have one or more projections 304 to contact inner surfaces of outer housing 102.

In use, inner housing 104 is placed in the outer housing 102 and guide wire is fed into the opening 101A of the inner housing 104. The wire insertion causes the inner housing to rotate and take up the guide wires. When dispensing guide wire, the pulling action causes the inner housing 104 to rotate, helping to dispense the guide wire.

Figure 4:
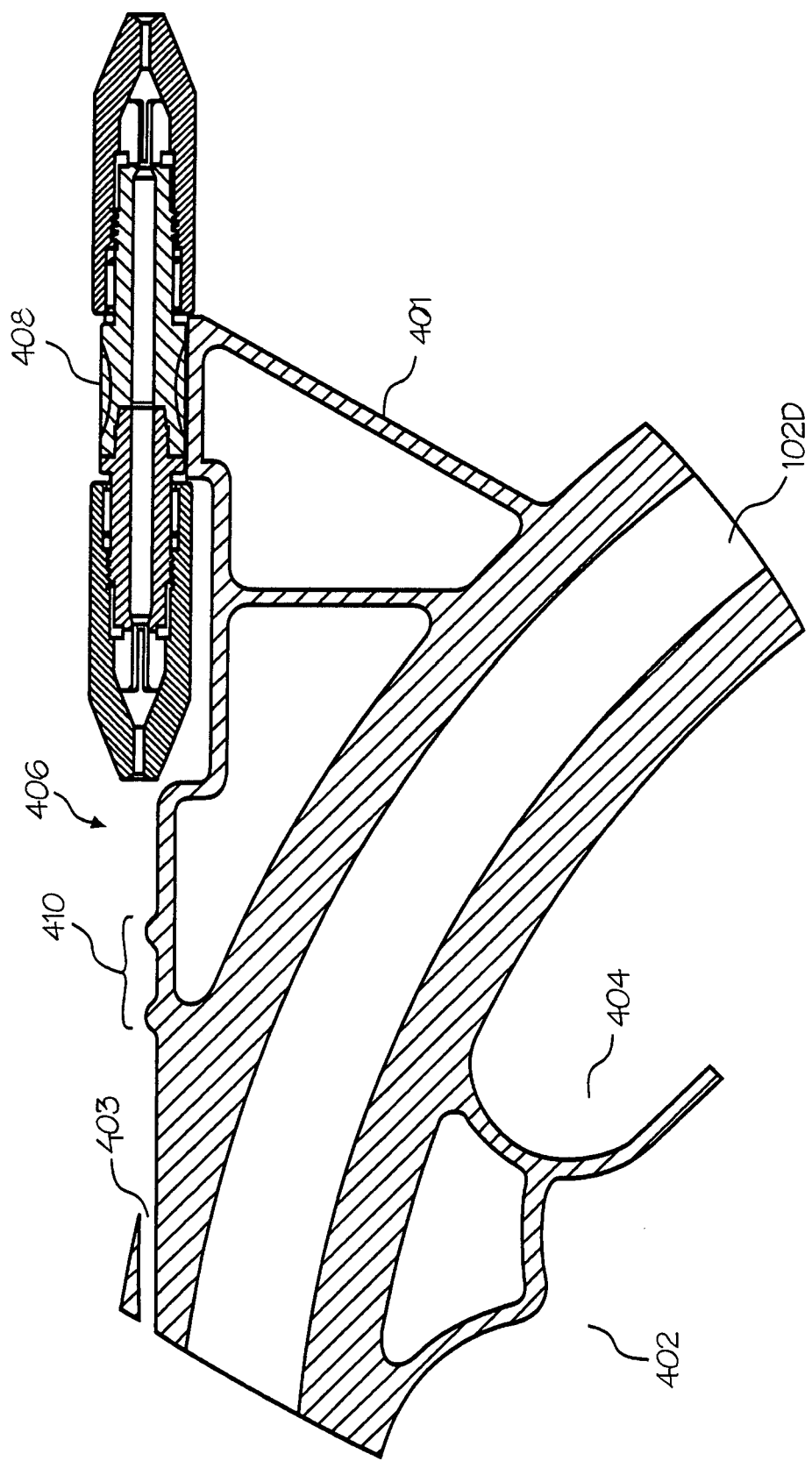
FIG. 4 is a view of preferred embodiments of the handle and bridge section of the device.

An optional handle 402 is shown in FIG. 4. There is a central section, which is part of outer housing 102 and possesses a lumen 403 for wire passage into the device and the stop of the race. Handle 402 as shown in FIG. 4, inside the center of the preferred device may have one or more of trigger guards 404 to restrain several fingers of the user. It has a bridge mechanism 406 to assist and simplify guide wire extraction. As the guide wire passes out from outer housing 104 it passes over a bridge section 406 of the device. The guide wire may then enter the wire torque device 408, if such a device is mounted to device 100. By providing such an arrangement, unwanted movement of these fingers is arrested during thumb movements and overall there will be less motion artifact of the RACE wire transport/delivery system.

Bridge section 406 has two small ridges 410 designed to trap the guide wire between the users thumb and the ridges. The guide wire is trapped in this location and while the thumb is moved forward the guide wire will then extrude out from race 104 without resistance. Optionally, bridge section 406 may exist between the double collets of the dual grip torque device. The guide wire then optionally enters the dual action, bi-directional, wire torque device 408. An example of a wire torque device is disclosed in co-pending U.S. application Ser.

No. 10/444,773, filed May 24, 2003 entitled Guide Wire Torque Device, the disclosure of which is incorporated by reference.

Figure 5:
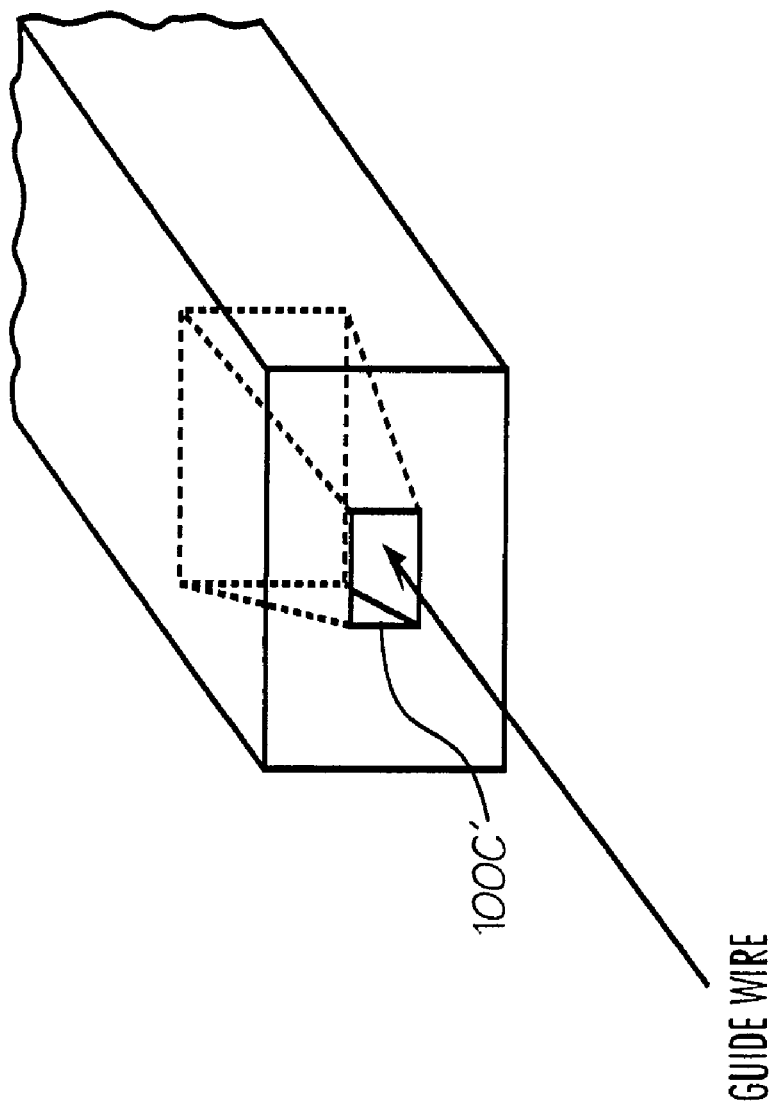
FIG. 5 shows an alternate opening 100C.

FIG. 5 shows an alternate opening 100C—that may be used with the invention. Opening 100c—flows into a larger opening to allow the guide wire to be placed in different locations in cavity 102D as race 104 moves.

Figure 6:
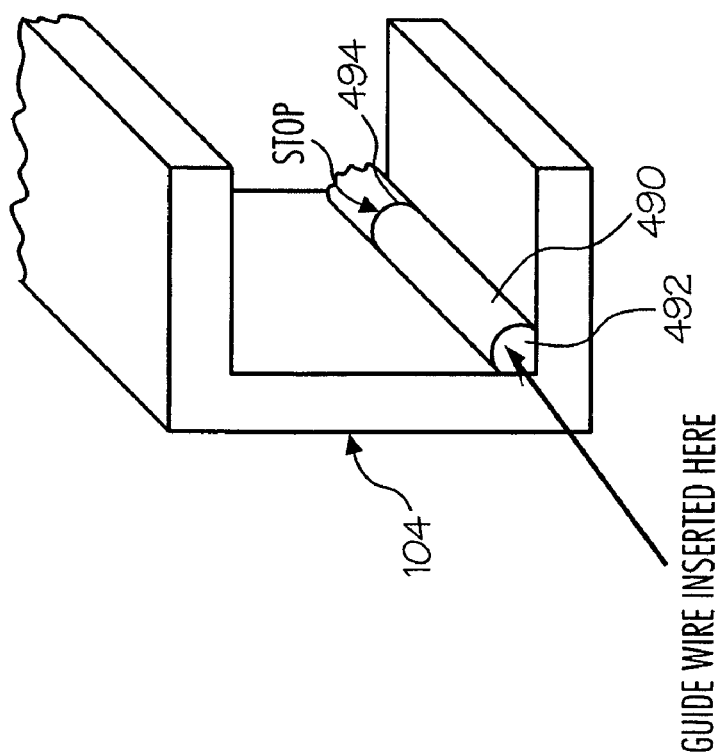
FIG. 6 shows a race according to the invention with a stop.

FIG. 6 shows a stop 490 on race 104. Stop 490 is for receiving a guide wire and transmitting force to the race and may be of any configuration and located in any position suitable for this purpose. As shown, stop 490 has an opening 492 and a physical stop 494 that the guide wire butts against.

Figure 7:
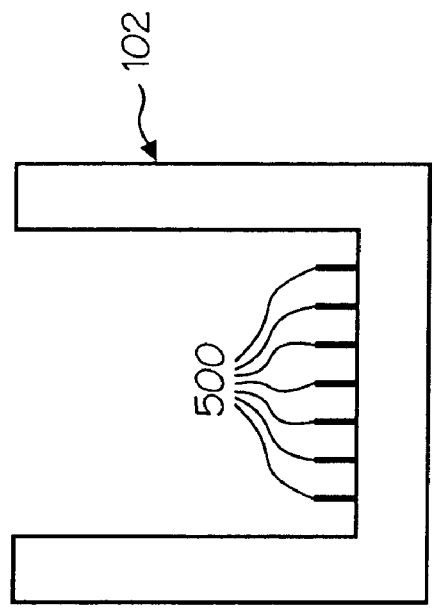
FIG. 7 shows an alternate raceway according to the invention.

FIG. 7 shows an alternate raceway 102 that has fingers 500 for separating different sections of the guide wire as it is received in raceway 102, and any suitable structure may be used for this purpose.

Figure 8:
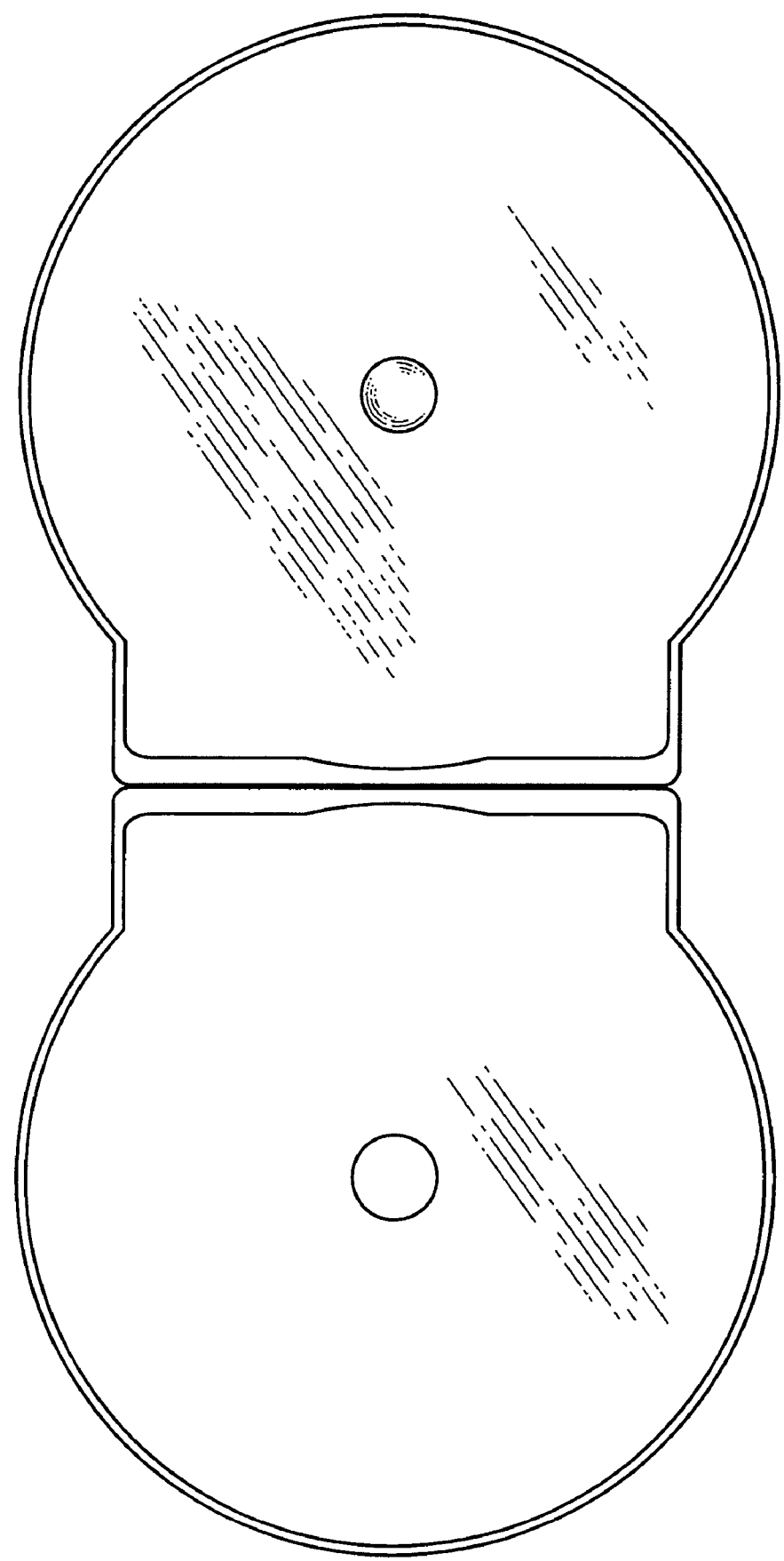
FIG. 8 shows, in accordance with an exemplarily embodiment of the present invention, a device body similar to a CD Jewel case.
Figure 9:
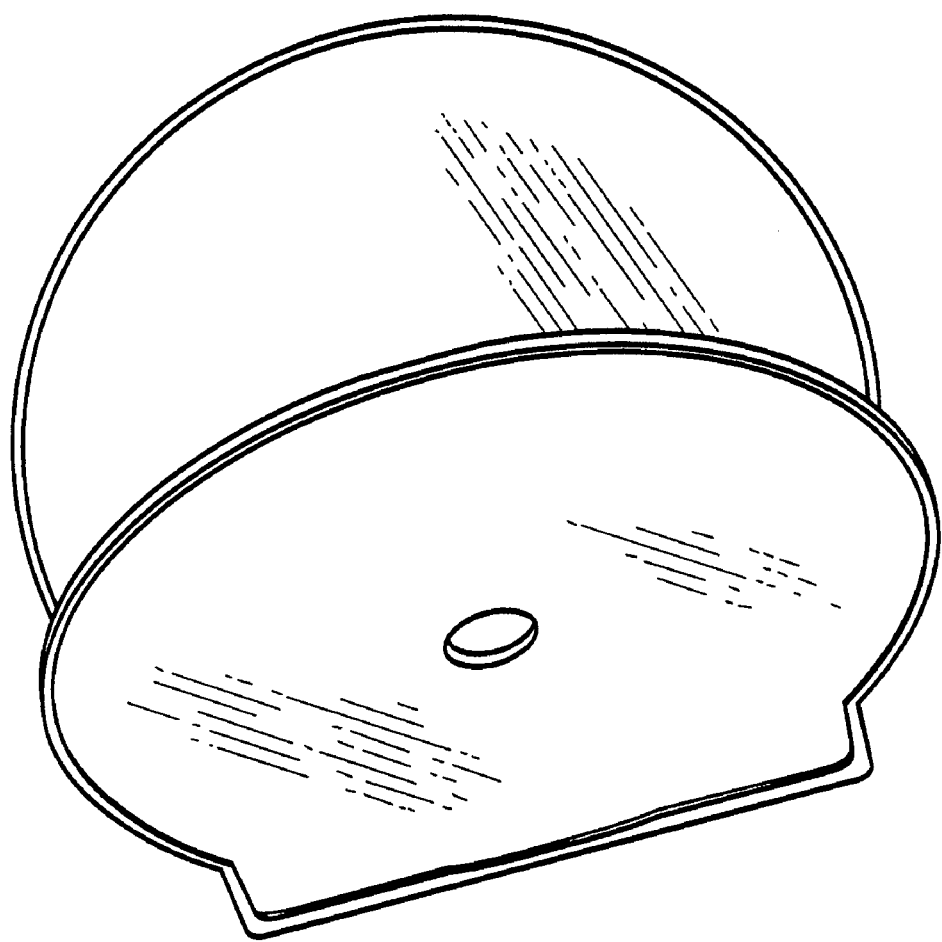
FIG. 9 shows, in accordance with an exemplarily embodiment of the present invention, a device body similar to a CD Jewel case.

The present invention thus provides several functions that have not been achievable previously. The system, due to the fact that it has a turnable race, which allows the wire to wound on to provides for a very compact wire-winding requirement. The current systems vary from a small spiral containing wire that is about 6 inches in diameter to spirals that are larger than 12 inches in diameter. According to exemplary embodiments of the present invention as illustrated in FIGS. 8-10, the race device of this invention may be able to pack guide wires into a body similar in size to a CD Jewel case.

Further, it may be possible to automate guide wire loading using such a device. Secondly, the race system significantly diminishes the storage volume requirements for guide wires. The preferred embodiment should be about 4½" to 5" square or 4½" to 5" in diameter, if round, and less than ½" thick. In addition to these features, the race device could be machine loaded with a second short opening wire if a duplex wire load is considered desirable by the user (typically a physician). Each wire could be extracted and re-loaded with relative ease. Concepts such as an aortogram wire pack, a carotid wire pack, a renal wire pack, a contra-lateral extremity wire pack or a coronary angiogram/PTCA/stenting wire pack for example could be designed and supplied.

Finally, due to the body it would be possible to label and bar code these devices. That would allow a wire dispenser cabinet system that could have a touch sensitive computer screen. The interventionalist could enter his/her code and then the bar code for the particular wire desired. The dispenser would drop the selected wire from a magazine and the wire could then be used. This system is not unlike jukeboxes of yester-year or today's Pixus system for dispensing drugs. Such a system could provide automatic on-line inventory control and management, both for the medical facility and the supplier of medical guide wires.

Having now described preferred embodiments of the invention, modifications and variations to the present invention may be made by those skilled in the art. The invention is thus not limited to the preferred embodiments, but is instead set forth in the following claims and legal equivalents thereof.

What is claimed is:

1. A guide wire container comprising:
   a raceway comprising an interior opening for storing at least one guide-wire and at least one projection within said raceway;
   at least one race/inner housing, wherein the race/inner housing comprises an outer surface capable of moving along the interior opening of said raceway, an inner surface capable of coupling to at least one guide wire, and at least one groove on said outer surface that at least partially receives said projection within said raceway; and
   at least one opening in said raceway for inserting at least one guide wire.

2. A guide wire container comprising:
   a raceway comprising an interior opening for storing at least one guide-wire;
   at least one race/inner housing, wherein the race/inner housing comprises an outer surface capable of moving along the interior opening of the raceway, an inner surface capable of coupling to at least one guide wire, and a stop on said inner surface of said race/inner housing, wherein force is transmitted from the guide wire to said stop to move said race/inner housing; and
   at least one opening in the raceway for inserting at least one guide wire.

3. The device of claim 1, wherein the stop comprises a cylindrical channel.

4. The device of claim 2, wherein the cylindrical channel is funnel shaped.

5. A guide wire container comprising:
   a raceway comprising an interior opening for storing at least one guide-wire and at least one groove within said raceway;
   at least one race/inner housing, wherein the race/inner housing comprises an outer surface capable of moving along the interior opening of said raceway, an inner surface capable of coupling to at least one guide wire, and at least one projection on said outer surface configured to interface with said groove within said raceway; and
   at least one opening in said raceway for inserting at least one guide wire.

* * * * *